United States Patent [19]

Sackner

[11] 4,452,252

[45] Jun. 5, 1984

[54] NON-INVASIVE METHOD FOR MONITORING CARDIOPULMONARY PARAMETERS

[75] Inventor: Marvin A. Sackner, Miami Beach, Fla.

[73] Assignee: Respitrace Corporation, Ardsley, N.Y.

[21] Appl. No.: 266,850

[22] Filed: May 26, 1981

[51] Int. Cl.³ ........................... A61B 5/02; A61B 5/08
[52] U.S. Cl. .................................. 128/671; 128/694; 128/721
[58] Field of Search ........ 128/693, 694, 713, 721–723, 128/725, 688, 670, 671, 716, 687, 689, 774

[56] References Cited

U.S. PATENT DOCUMENTS

| | | | |
|---|---|---|---|
| 3,340,867 | 9/1967 | Kubicek et al. | 128/713 |
| 3,742,936 | 7/1973 | Blanie et al. | 128/723 |
| 4,306,567 | 12/1981 | Krasner | 128/671 |
| 4,308,872 | 1/1982 | Watson et al. | 128/721 X |

FOREIGN PATENT DOCUMENTS 2802770 7/1978 Fed. Rep. of Germany ...... 128/716

*Primary Examiner*—Lee S. Cohen
*Attorney, Agent, or Firm*—Hubbell, Cohen, Stiefel & Gross

[57] ABSTRACT

A method for monitoring cardiopulmonary events is disclosed. The basic method comprises looping an extensible conductor (14) in close encircling relation about the neck (12) of the subject (10), providing a signal indicative of the inductance of the loop, and monitoring the signal. This signal contains both qualitative and quantitative cardiopulmonary information. In accordance with another aspect of the method, an extensible conductive loop (14) is disposed in close encircling relation about the head such that the plane defined by the loop extends through the mouth. By providing a signal indicative of changes in the inductance of the loop, qualitative and quantitative information for mouth volume may be obtained.

26 Claims, 15 Drawing Figures

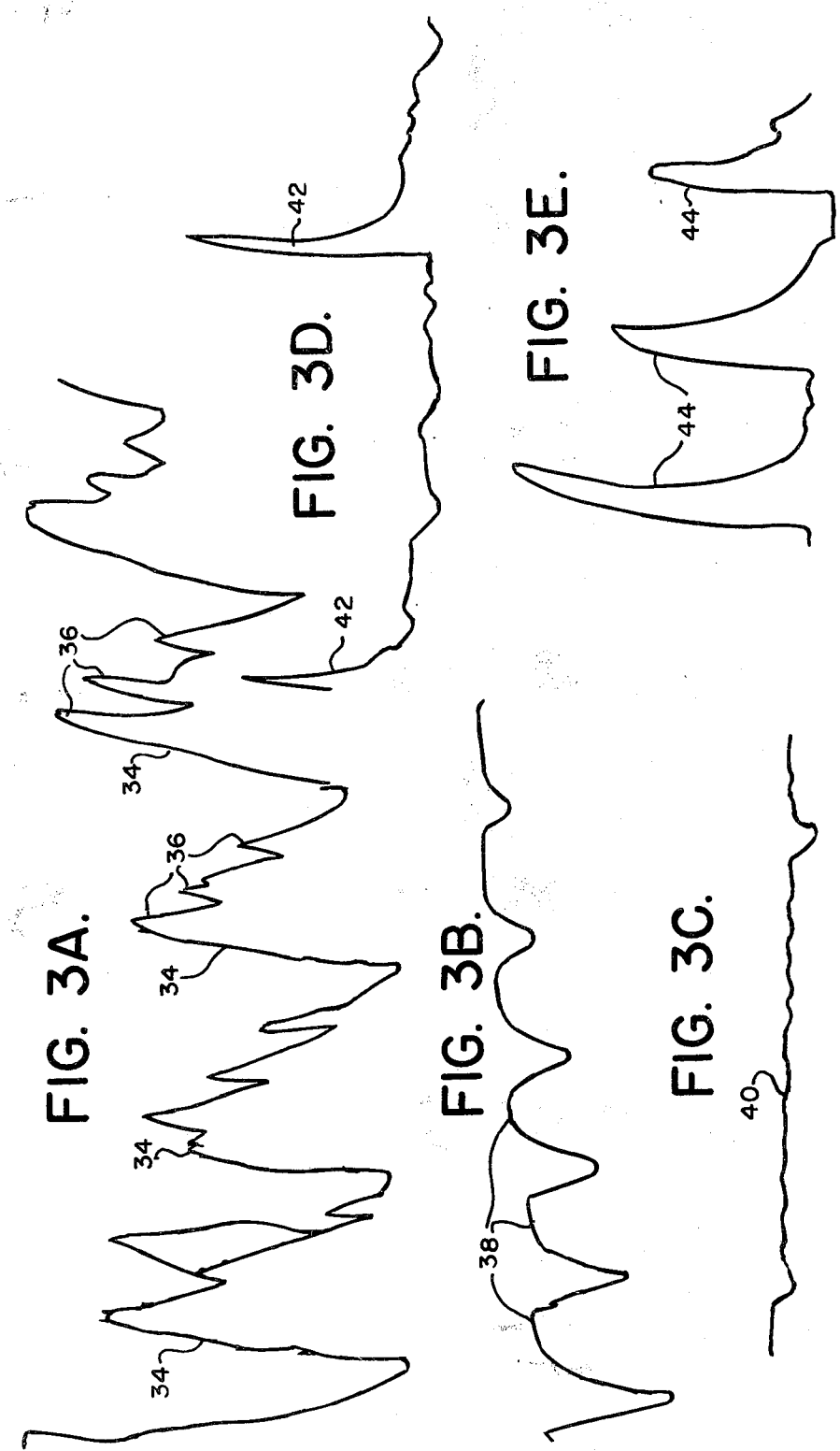

FIG. 3F.
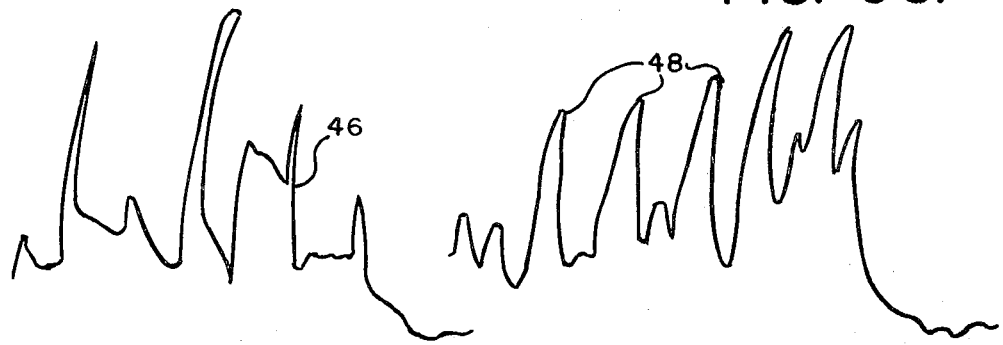
FIG. 3G.
FIG. 3H.
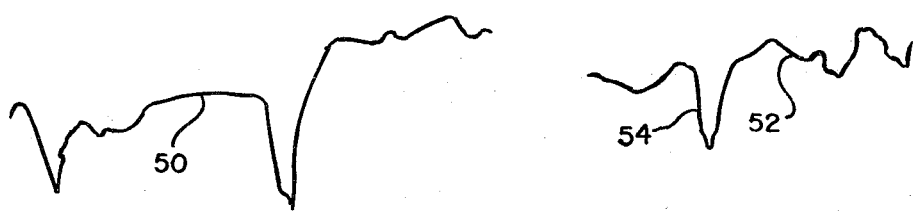
FIG. 3I.
FIG. 3J.
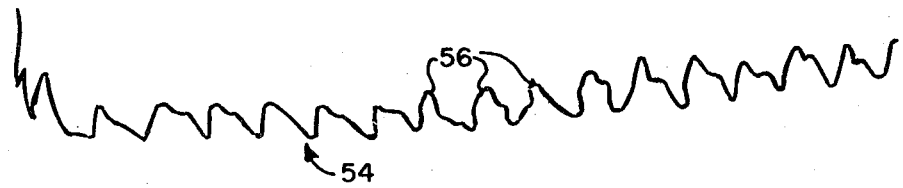

NON-INVASIVE METHOD FOR MONITORING CARDIOPULMONARY PARAMETERS

TECHNICAL FIELD

This invention pertains to non-invasive monitors of cardiopulmonary parameters.

BACKGROUND ART

Apparatus and methods for monitoring cardiopulmonary parameters are, of course, well known, and some such apparatus and methods are non-invasive. Cardiopulmonary monitoring is clinically useful, for example, in intensive care units and other applications. Despite the existence of cardiopulmonary monitors in the prior art, it would be highly desirable to provide a simplified cardiopulmonary monitor which does not substantially restrict patient movement, thereby rendering the monitor more suitable for long term use. Also, applicant is not aware of any prior art monitoring techniques which employ a single transducer element to monitor both cardiac and pulmonary parameters.

BRIEF DESCRIPTION OF THE DRAWINGS

In the drawings:

FIGS. 3A-3J are tracings obtainable on a strip chart recorder when the method of the present invention is practiced;

DISCLOSURE OF THE INVENTION

Figure 1:
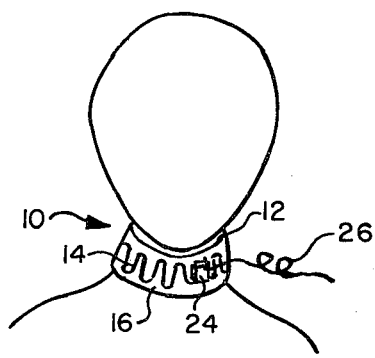
FIG. 1 is a perspective view showing a portion of the system for monitoring cardiopulmonary parameters in accordance with the method of the present invention.

According to the present invention, I have found that various cardiopulmonary events may be monitored by monitoring changes in the cross-sectional area of the neck, or by monitoring a parameter indicative of changes in cross-sectional area. In accordance with the preferred basic method of the present invention, an extensible conductor is looped in close encircling relation about the neck, and suitable circuitry is provided for measuring changes in the inductance of the loop, the changes in inductance being proportional to the changes in cross-sectional area of the neck. The resulting signal, which may be recorded on a strip chart recorder or CRT, contains both cardiac and pulmonary information.

More specifically, the cardiac portion of the signal comprises the carotid pulse, which may be isolated by time series averaging or appropriate filtering. Likewise, the pulmonary portion of the signal may also be isolated by time series averaging or appropriate filtering. The pulmonary signal may be analyzed for time related respiration parameters, such as respiration rate, and inspiration and expiration times. The pulmonary signal may also be analyzed for specific pulmonary events, such as snoring, coughing, apneas, swallows, etc. These events produce characteristic deflections or patterns which may be automatically monitored by suitable circuitry for effecting level detection, rate detection or pattern recognition. I have also found that the pulmonary component of the signal may be calibrated to provide a signal semiquantitatively related to intrapleural pressure. For example, an esophageal balloon catheter may be employed to effect calibration.

In accordance with another aspect of the method in accordance with the present invention, I have found that changes in mouth volume as well as absolute mouth volume may be detected by looping an extensible conductive element about the head such that the plane defined by the loop extends through the mouth. If this is done, a signal indicative of changes in the inductance of the loop provides qualitative information as to mouth volume. This information may be quantified, both for changes in the mouth volume and for absolute mouth volume, by calibrating the signal. This aspect of the invention is particularly useful for obtaining information regarding puff volume and the proportion of smoke inhaled relative to total respiration volume.

The above as well as further aspects of the methods in accordance with the present invention will become more fully apparent from the following detailed description and annexed drawings of the presently preferred best modes thereof.

BEST MODE FOR CARRYING OUT THE INVENTION

In accordance with one aspect of the method in accordance with the present invention, an extensible electrically conductive loop is disposed and held in close encircling relation about the neck. The ends of the loop are connected to circuits capable of providing a signal indicative of the changes in the self-inductance of the loop, which is in turn proportional to the changes in cross-sectional area enclosed by the loop. By suitably processing the signal, a number of cardiopulmonary parameters may be obtained.

Referring now to FIG. 1, the extensible electrically conductive loop 14 disposed in close encircling relation about the neck 12 of the subject 10 is preferably supported in any suitable fashion on an elastic tube 16 or the like. The tube 16 preferably has two free ends (not shown) which may be releasably connected, as by Velcro strips, to facilitate placement about the neck 12. The conductive loop 14 is rendered extensible by, for example, forming the loop in alternating up and down looplets advancing in a plane. Numerous other configurations for rendering a conductive loop extensible, and for securing the conductive loop to a tubular stretch bandage or the like, are disclosed in commonly assigned application Ser. No. 102,408, entitled Method and Apparatus for Monitoring Respiration, filed Dec. 11, 1979, now U.S. Pat. No. 4,308,872 the contents of which are hereby incorporated herein by reference in their entirety. Changes in the cross sectional area of the neck portion enclosed by the conductive loop 14 cause the elastic tube 16 and conductive loop 14 to expand and contract, which results in corresponding changes in the cross sectional area and hence in the inductance of the loop. As explained below, if the inductance of the loop 14 is converted to an electrical signal, a number of cardiopulmonary parameters for the subject 10 may be obtained.

Figure 2A:
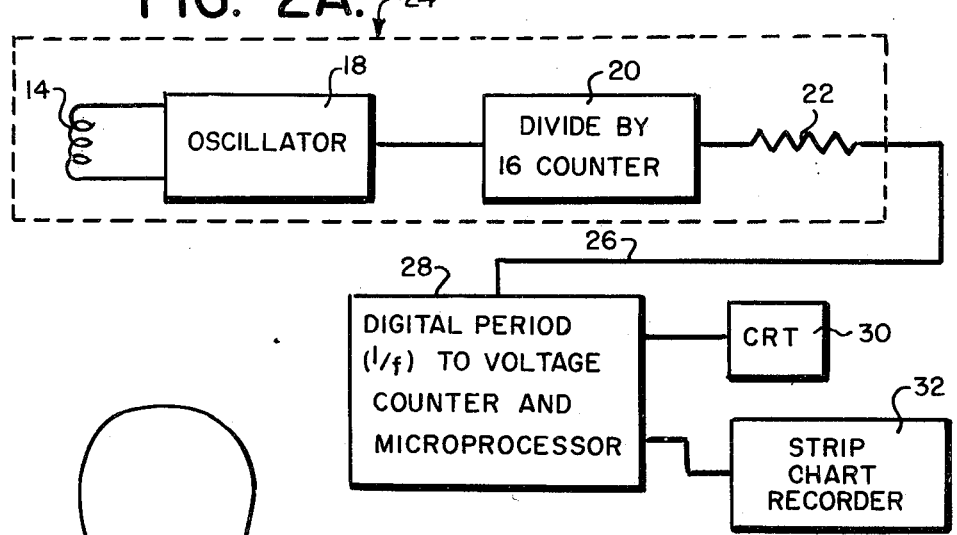
FIG. 2A is a block diagram showing the full system for monitoring cardiopulmonary parameters in accordance with the method of the present invention.

Referring now to FIG. 2A, the preferred circuitry for converting the inductance of the loop 14 to a suitable electrical signal is diagrammatically illustrated. As shown, a variable frequency oscillator 18 is connected to the ends of the conductive loop 14. The resonant frequency of the oscillator is determined by an internal capacitor and the inductance of the conductive loop 14. This frequency may, for example, be centered about 300 KHz and will vary as the loop 14 expands and contracts. The output of the oscillator is connected to a conventional divide by sixteen counter 20 which reduces the frequency of the signal from the oscillator to minimize interference during subsequent signal transmission. As shown, the output of the counter 20 is preferably coupled to a resistor 22 which converts the voltage signal at the output of the counter 20 to a corresponding current signal, the purpose again being to minimize interference during signal transmission. To minimize artifacts, the electronics for the oscillator 18 and counter 20 as well as the coupling resistor 22 are preferably incorporated in a module 24 secured in any suitable fashion to the tubular bandage 16 on the neck 12 of the subject 10 (FIG. 1).

The current signal at the output of the coupling resistor 22 is connected via a suitable cable 26 to signal processing circuitry identified in FIG. 2A by the box 28. The box 28 incorporates a digital period (1/f) to voltage converter which provides a voltage signal whose amplitude varies in response to the period of the signal at the output of the counter 20. As will be more fully explained below, the circuit represented by the box 28 preferably also incorporates a microprocessor for processing the voltage signal to yield certain types of usable information. The thus processed signal may then be displayed on one or more suitable output devices, shown by way of example in FIG. 2A as a CRT terminal 30 and a strip chart recorder 32.

Figure 2B:
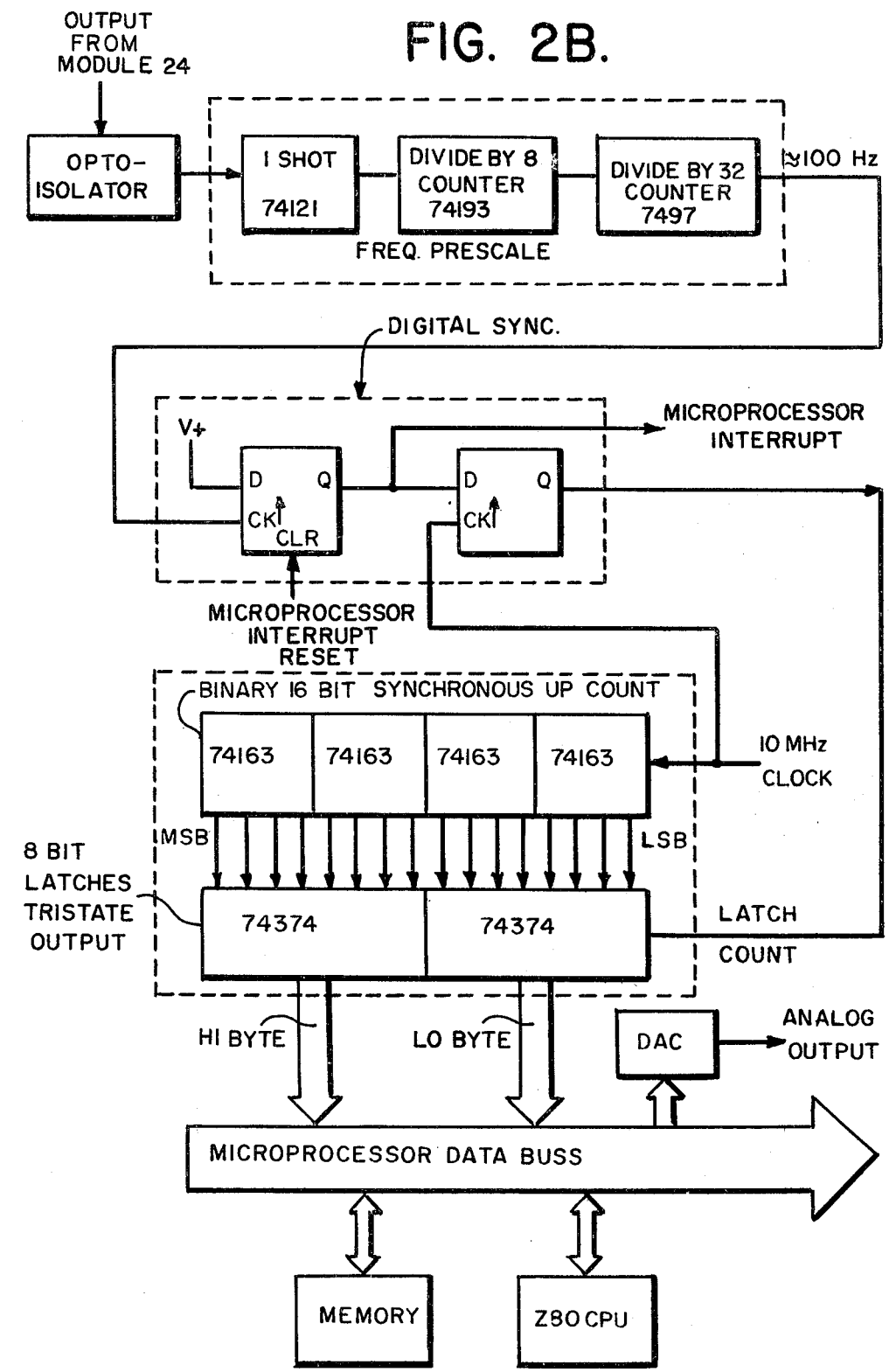
FIG. 2B is partially schematic, partially diagrammatic representation of a portion of the system illustrated in FIG. 2A.

Suitable circuits for the oscillator 18 and counter 20 are available in the prior art. For example, a suitable circuit for the oscillator 18 is disclosed in above-mentioned U.S. Pat. No. 4,308,872. The counter 20 may comprise the National Semiconductor CD4020. While prior art circuits are also available for accomplishing the functions attributed to the box 28, a particular digital circuit has been developed for use with this invention which enhances the quality of the output signal. A schematic for the preferred digital circuit represented by the box 28 in FIG. 2A is shown in FIG. 2B. The construction and operation of the circuit of FIG. 2B will be readily apparent to those skilled in the art.

Referring now to FIG. 3, tracings obtainable on the strip chart recorder 32 in accordance with the method of the present invention are shown. Referring first to FIG. 3A, an AC coupled amplified unfiltered signal from the output of the box 28 in FIG. 2A is illustrated. In FIG. 3A, each large, irregularly shaped deflection 34 comprises one breath of the subject 10, whereas the smaller deflections 36, which are most visible on the descending portion of the deflections 34, comprise the carotid arterial pulse. As the signal at the output of the box 28 is a real time signal, it will be immediately apparent that even the unfiltered signal illustrated in FIG. 3A contains clinically useable cardiopulmonary information. For example, both the pulse rate and breath rate for the subject 10 are readily visually observable in FIG. 3A. As explained below, for particular applications the quality of the signal may be improved by appropriate filtering. In FIG. 3A, base line drift results because the circuit of FIG. 2B is used in its AC coupled mode. However, and as will be apparent from the circuit of FIG. 2B, DC coupling is also possible.

As noted, the smaller deflections in FIG. 3A represent the carotid pulse, and it is apparent from FIG. 3A that the carotid pulse frequency exceeds respiration frequency. Accordingly, the respiration signal may be "cleaned up" by low pass filtering or, alternatively, time series averaging may be used, as will be explained below. Low pass filtering is preferably accomplished by the microprocessor incorporated in the circuit of FIG. 2. Suitable programming for the microprocessor to accomplish filtering is well within the capabilities of the skilled art worker. Referring to FIG. 3B, the signal at the output of the box 28 in FIG. 2A after suitable low pass filtering to remove the carotid pulse is shown. In FIG. 3B, each deflection 38 comprises one breath of the subject 10. The gain setting on the strip chart recorder for FIGS. 3A and 3B was the same. Again, base line drift is due to the fact that the device is AC coupled. It will be apparent that the tracing of FIG. 3B may be analyzed to yield the usual time related respiration parameters, e.g. respiration rate, inspiration time and expiration time.

Referring now to FIG. 3C, which was recorded with the same gain setting as for FIGS. 3A and 3B, and which was also filtered to remove the carotid pulse component, a trace corresponding to artificially induced apnea is shown. It is readily apparent from FIG. 3C that during apnea, the amplitude of the respiration signal 40 is vastly reduced as compared with the normal respiration signal of FIG. 3B. It will therefore be apparent that the cardiopulmonary monitoring method in accordance with the present invention may be used to detect apneas by low pass filtering the output signal, and then processing that signal through level detection circuitry to provide a suitable warning signal, e.g., aural or visual, when the amplitude of the respiration signal decreases below a predetermined level for a predetermined time period. Suitable level detection circuitry for this application will be well within the capabilities of the skilled art worker once this description is known.

Referring to FIG. 3D, coughs produce a signal characterized by large rapid upward deflections 42. In FIG. 3D, as well as FIGS. 3E-3G, the gain setting on the strip chart recorder was the same as that used for FIGS. 3A-3C. Also, in FIG. 3D, as well as FIGS. 3E-3G, the signals have been filtered to remove the carotid pulse component.

FIG. 3E shows a tracing taken with the subject 10 snoring, which also produces a signal characterized by large upward deflections 44 if the coil is placed at the upper portion of the neck above the larynx. A downward deflection is produced if the coil is placed about the lower portion of the neck below the larynx. FIG. 3F shows the characteristic signal 46 resulting from jerking movements of the neck 12 of the subject 10. FIG. 3G is a tracing taken with the subject's airway obstructed. The characteristic rapid deflections 48 in FIG. 3G show the subject 10 gasping for air.

FIG. 3H shows a signal 50 which results from talking. The strip chart recorder 32 was set for a reduced gain for the tracing of FIG. 3H as compared with the gain settings used for the tracings of FIGS. 3A-3G.

The tracing shown in FIG. 3I, which was taken with the same gain setting used for FIG. 3H, shows the signal 52 obtained when the subject 10 swallows. Note that a swallow results in a characteristic negative deflection 54.

It will thus be apparent that in addition to time related respiratory parameters, the method of the invention yields a wide variety of qualitative information. Thus, apneas, obstructions, coughs, snoring, and swallows may all be monitored, and specific events may be detected by employing means, such as appropriate circuitry, for effecting level detection, rate detection and/or pattern recognition.

Where time related respiration parameters are to be monitored over extended periods, it is presently preferred to employ time series averaging to eliminate the effect of artifacts resulting, for example, from neck movement. Basically, information from a plurality of breaths are averaged over a predetermined time interval, for example, one minute, and then the respiration parameters are derived from the average. Since clinically significant changes in time related breath parameters do not generally occur in less than one minute, the probability of losing significant data is minimal. In any event, if desired, both the averaged signal and the continuous signal may be simultneously monitored. Preferably, the microprocessor incorporated in the circuit of FIG. 2 is programmed for time series averaging. As such programming will be well within the capabilities of the skilled art worker once this description is known, a further description thereof is unncessary. It is also possible to obtain respiration parameters by time series averaging the unfiltered signal shown in FIG. 3A. If this is done, an appropriate trigger signal could be obtained by differentiating the respiration signal available at the output of the system disclosed in U.S. Pat. No. 4,308,872.

Referring again to FIGS. 1 and 2, the system may be calibrated to yield a signal semi-quantitatively related to intrapleural pressure. Preliminary experiments indicate that calibrations for quiet and deep breathing may differ from rapid expiratory events such as coughing. It is proposed to employ an esophageal balloon catheter during the calibration process. To effect calibration, the subject first swallows the esophageal balloon catheter, and then takes quiet and deep breaths and coughs with different efforts. During breathing and coughing, signals are simultaneously recorded for the neck coil 14 and the pressure at the esophageal balloon, the latter corresponding to intrapleural pressure. Based on these readings, the circuitry of FIG. 2 is calibrated to provide an output signal which is semi-quantitatively related to intrapleural pressure during these two events, i.e. breathing and coughing. Once calibration is complete, the esophageal balloon catheter is removed, whereupon intrapleural pressure may be detected from the neck coil signal alone.

Alternatively, it may be possible to obtain calibration values by having the subject make graded inspiratory efforts or graded expiratory efforts against a closed airway. Under these circumstances, i.e. closed airway, mouth pressure equals alveolar pressure which closely approximates intrapleural pressure. Thus, breathing can be calibrated from inspiratory efforts and coughing from expiratory efforts utilizing mouth pressure. Finally, changes in intrapleural pressure may be assumed as a percent change from base line if it can be demonstrated that there is a linear or predictable relation between intrapleural pressure and breathing or coughing thus obviating the need for placement of the esophogeal balloon catheter.

Referring again to FIG. 3A, when the signal component comprising the carotid pulse is of interest, the respiration portion of the signal may be removed by high pass filtering. Again, such high pass filtering is preferably carried out by the microprocessor incorporated in the circuit of FIG. 2, and as suitable programming will be will within the capabilities of the skilled art worker once this description is known, a further description thereof is unnecessary. A high pass filtered signal 54 showing only the carotid pulse is illustrated in FIG. 3J, wherein each deflection 56 comprises one pulse beat. It will immediately be apparent that pulse rate of the subject 10 is readily determinable from FIG. 3J. Where pulse rate is to be monitored on a long term basis, the time series averaging technique discussed above may be used to eliminate "noise" resulting, for example, from jugular vein or movement artifacts. Time series averaging would also be effective to obtain the pulse rate from the unfiltered signal shown in FIG. 3A. This is possible because the breath deflections 34 and carotid pulse deflections 36 are not time related. Consequently, if data storage is triggered from, for example, the R-wave portion of the electrocardiogram, the breath deflections will cancel out over time.

The carotid pulse signal obtained in accordance with the method of the present invention may be used with a phonocardiogram and an EKG, to obtain systolic time intervals in accordance with well known techniques. The nature of the transducer employed in connection with the method of the present invention for obtaining the carotid pulse, as compared with prior art transducers, enhances the results, especially with subject movement, such as occurs during exercise.

Figure 4:
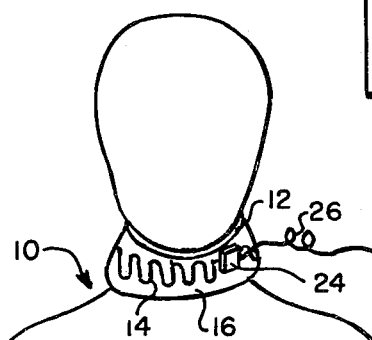
FIG. 4 is a view similar to FIG. 1 showing how to employ the method of the present invention for measuring arterial pulse wave velocity.
Figure 4:
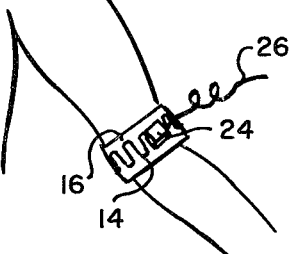

Referring now to FIG. 4, arterial pulse wave velocity may be detected by comparing the carotid pulse signal with, for example, a brachial pulse signal. As shown, the brachial pulse is preferably obtained by employing a transducer substantially identical to the one disposed about the neck, save for the fact that it is slightly smaller. Arterial pulse wave velocity may be obtained by detecting the time differences between the carotid and brachial pulse signals, the brachial pulse signal preferably being obtained by employing the circuitry of FIG. 2. For example, the time differential between the upstroke of the carotid and brachial pulses may be used. Of course, pulse sites other than the brachial artery may be employed for this purpose. For example, the radial pulse or a finger pulse may be used.

It will now be apparent that both cardiac and pulmonary parameters can be simultaneously monitored by splitting the output signal from the coil 14 into two separate signals, and then processing one signal to yield pulmonary parameters, and the other to yield cardiac parameters, all as is more fully explained above. Alternatively, two separate coils 14 could be disposesd about the neck with the signal from each coil being separately processed. The two coil technique could also be employed for intrapleural measurements, where it is expected that calibration will be different for breathing and rapid expiratory events.

Figure 5:
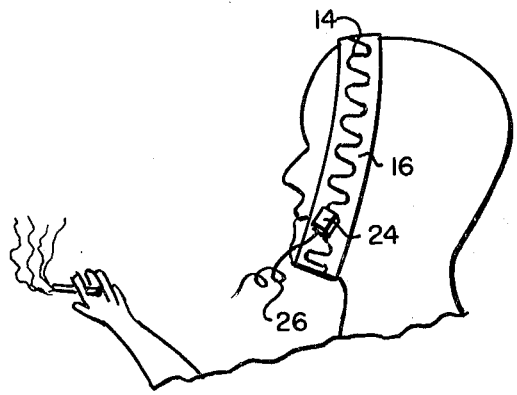
FIG. 5 is a view similar to FIG. 1 showing another aspect of the method in accordance with the present invention.

Referring now to FIG. 5, in accordance with another aspect of the method in accordance with the present invention, changes in the mouth volume of the subject 10 may be monitored. As shown in FIG. 5, this is accomplished by disposing the extensible electrically conductive loop 14 vertically about the head such that the plane defined by the coil passes through the subject's mouth. As shown in FIG. 5, this is preferably accomplished by disposing the coil 14 around the front part of the subject's head and under the chin. Preferably, the coil 14, tube 16 and module 24 are of the same construction as that illustrated and described above in connection with FIG. 1. Likewise, the circuitry used for processing the inductance signal from the conductive loop 14 is preferably identical with that illustrated in FIG. 2. If desired, an elastic band (not shown) may be disposed about the head in the vicinity of the forehead for holding the loop 14 and tube 16 in place.

Changes in mouth volume due to particular events, such as tongue movement, results in characteristic signals which may be recorded on the strip chart recorder 32. Monitoring changes in mouth volume in accordance with the method of the present invention may be clinically useful for detecting lack of rhythmic movements of the tongue synchronous with inspiration as occurs in the obstructive sleep apnea syndrome.

The device illustrated in FIG. 5 may be calibrated to measure absolute volumes or differential volumes. To calibrate for absolute volumes, the coil 14 is preferably first placed about two forms having different known volumes, whereupon the circuitry of FIG. 2 may be calibrated based on the resulting readings. For differential volume calibration, the device may be calibrated directly on the subject based on known quantities of mouth volume. For example, the subject can be instructed to suck in air from a sensitive spirometer with graded efforts as in puffing on a cigarette. When calibrated, the measurement obtainable with the head coil over 10–100 ML volumes is ±10% of the measurement taken with a sensitive spirometer. Still referring to FIG. 5, it is possible to measure the volume of smoke puffed during smoking. To do so, it is only necessary to measure the difference between the volume in the mouth before and after e.g. a cigarette puff. This information can also be used to determine the amount of smoke inhaled into the lungs relative to total tidal volume. Thus, when a person first puffs on a cigarette, only smoke is initially drawn into the mouth. Accordingly, the cigarette puff is characterized by a generally increasing output signal from the face coil, which eventually levels off at the end of the puff. The mouth volume at the end of the puff is recorded. Once the puff is complete, the subject typically then inhales the smoke in the mouth, together with the additional air into the lungs. The total tidal volume (smoke and air) may be measured in accordance with any one of a variety of known techniques, but preferably the technique disclosed in the above-mentioned U.S. Pat. No. 4,308,872. Since the volume of inhaled smoke has already been recorded, the proportion of smoke inhaled relative to total respiration volume may be determined by dividing the volume of smoke inhaled by total respiration volume. Also, the time of breath holding obtained from the system disclosed in U.S. Pat. No. 4,308,872 provides an index of the amount of smoke that might be deposited within the lungs. Finally, this method provides data on puff volume and flow profile which should be helpful in establishing standards for smoking machines used to assess the quantity of tar and nicotine in cigarettes.

Once the foregoing is known, it will be apparent that the presently preferred best modes for practicing the methods in accordance with the present invention may be modified in several respects. For example, while the above method has been described in connection with human subjects, those skilled in the art will appreciate that it may be employed with certain animal subjects as well. Also, while it is presently preferred to measure changes in the cross-sectional area of the neck and head by measuring the changes in the inductance of a conductive loop, this is not essential. Thus, because changes in the cross-sectional area in the neck and head are relatively small, changes in circumference could be measured in lieu of changes in cross-sectional area, as the two are substantially proportional for small changes. Similarly, changes in volume, which will be proportional to changes in cross-sectional area, could also be measured. Accordingly, in the following claims, the phrase "detecting changes in cross-sectional area or a parameter indicative thereof" should be understood to include cross-sectional area per se, as well as circumference and volume, both of which are proportional to cross-sectional area as exlained above.

Since these as well as further changes and modifications are intended to be within the scope of the present invention, the above description should be construed as illustrative and not in the limiting sense, the scope of the invention being defined by the following claims.

I claim:

1. A method for non-invasively monitoring one or more cardiopulmonary events in a subject comprising:
   disposing about the neck means for detecting changes in cross-sectional area or a parameter indicative thereof;
   providing a signal indicative of the changes in cross-sectional area or a parameter indicative thereof as detected by said detecting means; and
   monitoring said signal, said signal being indicative of said cardiopulmonary events.

2. The method according to claim 1, wherein said disposing step comprises looping an extensible conductor in close encircling relation about the neck and wherein said signal providing step comprises measuring changes in the inductance of the conductive loop.

3. The method according to claim 2, wherein said monitoring step comprises processing said signal whereby to remove the carotid arterial pulse component, and monitoring said processed signal.

4. The method according to claim 3, wherein said processing step comprises low pass filtering said signal.

5. The method according to claim 4, further comprising time series averaging said signal.

6. The method according to claim 3, wherein said processing step comprises time series averaging said signal.

7. The method according to claim 3, further comprising calibrating said signal to provide a signal semi-quantitatively related to intrapleural pressure.

8. The method according to claim 7, further comprising looping an additional extensible conductor in close encircling relation about the neck, providing an additional signal indicative of the changes in the inductance of the additional conductive loop, processing the additional signal whereby to remove the carotid arterial pulse component, and calibrating said first mentioned signal and said additional signal for respiratory events having first and second frequencies, respectively.

9. The method according to claim 3, wherein said monitoring step comprises monitoring the amplitude of said signal to detect specific pulmonary events.

10. The method according to claim 3, wherein said monitoring step comprises monitoring the frequency of said signal to detect specific pulmonary events.

11. The method according to claim 3, wherein said monitoring step comprises monitoring the pattern of said signal to detect specific cardiopulmonary events.

12. The method according to claim 2, wherein said monitoring step comprises processing said signal whereby to remove the respiration component, and monitoring said processed signal.

13. The method according to claim 12, wherein said processing step comprises high pass filtering said signal.

14. The method according to claim 13, further comprising time series averaging said signal.

15. The method according to claim 12, wherein said processing step comprises time series averaging said signal.

16. The method according to claim 4, further comprising comparing said processed signal with signals from an EKG and phonocardiogram whereby to determine systolic time intervals.

17. The method according to claim 12, wherein said monitoring step comprises monitoring the amplitude of said signal to detect specific cardiac events.

18. The method according to claim 12, wherein said monitoring step comprises monitoring the frequency of said signal to detect specific cardiac events.

19. The method according to claim 12, wherein said monitoring step comprises monitoring the pattern of said signal to detect specific cardiac events.

20. The method according to claim 2, wherein said monitoring step comprises splitting said signal into first and second signals, processing said first signal whereby to remove the carotid arterial pulse component, processing said second signal whereby to remove the respiration component, and monitoring said processed first and second signals.

21. The method according to claim 2, further comprising looping an additional extensible conductor in close encircling relation about another portion of the body of said subject at the site of a pulse other than the carotid pulse;
providing an additional signal indicative of the changes in the inductance of the additional conductive loop; and
comparing the signal from the conductor looped about the neck with said additional signal whereby to determine arterial pulse wave velocity.

22. The method according to claim 21, wherein said other pulse is the brachial, radial or finger pulse.

23. The method according to claim 2, wherein said monitoring step comprises monitoring the amplitude of said signal to detect specific cardiopulmonary events.

24. The method according to claim 2, wherein said monitoring step comprises monitoring the frequency of said signal to detect specific cardiopulmonary events.

25. The method according to claim 2, wherein said monitoring step comrpises monitoring the pattern of said signal to detect specific cardiopulmonary events.

26. The method according to claim 2, further comprising looping an additional extensible conductor in close encircling relation about the neck; providing an additional signal indicative of the changes in the inductance of the additional conductive loop; and wherein said monitoring step comprises processing said first-mentioned signal and said additional signal to remove, respectively, the carotid arterial pulse component and the respiration component, and monitoring said processed signals.

* * * * *